United States Patent [19]
Ammar et al.

[11] Patent Number: 5,885,276
[45] Date of Patent: Mar. 23, 1999

[54] METHOD AND DEVICE FOR TRANSMYOCARDIAL CRYO REVASCULARIZATION

[75] Inventors: Rony Ammar; Mordechai Bliweis, both of Haifa; Glinka Ofer, Kiryat Bialik; Gideon Even Sturlesi, Cammon, all of Israel

[73] Assignee: Galil Medical Ltd., Yokneam, Israel

[21] Appl. No.: 982,860

[22] Filed: Dec. 2, 1997

[51] Int. Cl.$^6$ .................................. A61B 17/36
[52] U.S. Cl. .................. 606/21; 606/22; 606/23
[58] Field of Search .............. 606/20–26; 62/51.2

[56] References Cited

U.S. PATENT DOCUMENTS

| | | | |
|---|---|---|---|
| 3,880,552 | 4/1975 | Sollami et al. | 62/293 |
| 5,007,099 | 4/1991 | Skertic et al. | 62/51.2 |
| 5,254,116 | 10/1993 | Baust et al. | 606/23 |
| 5,452,582 | 9/1995 | Longsworth | 62/51.2 |
| 5,522,870 | 6/1996 | Ben-Zion . | |
| 5,540,062 | 7/1996 | Maytal . | |
| 5,716,353 | 2/1998 | Matsuura et al. | 606/22 |
| 5,758,505 | 6/1998 | Dobak, III et al. | 62/6 |

FOREIGN PATENT DOCUMENTS

WO 96/37158  5/1995  WIPO .

OTHER PUBLICATIONS

Kohmoto et al, "Physiology, Histology, and 2–Week Morphology of Acute Transmyocardial Channels Made With a $CO_2$ Laser", *Ann. Thorac. Surg.*, 63: 1275–1283, 1997.

Horvath et al, "Transmyocardial Laser Revascularization: Results of a Multicenter Trial with Transmyocardial Laser Revascularization Used as Sole Therapy for End–Stage Coronary Artery Diseas", *J. Thoracic and Cardiovascular Surgery*, 113(4): 645–654, 1997.

Fisher et al, "Histologic Analysis of Transmyocardial Channels: Comparison of $CO_2$ and Holmium: YAG Lasaers", *Ann Thorac Surg*, 64: 466–472, 1997.

Lewis et al, "Angiogenesis by Gene Therapy: A New Horizon for Myocardial Revascularization?", *Cardiovascular Research*, 1997.

*Primary Examiner*—Michael Peffley
*Assistant Examiner*—Roy Gibson
*Attorney, Agent, or Firm*—Mark M. Friedman

[57] ABSTRACT

Cryosurgery method and device for performing trans myocardial revascularization are provided. The method includes: forming trans myocardial channels by cryoablating selected portions of the myocardial tissue. The cryosurgery device includes:(a) an operating member having an operating surface and a hollow; and a housing member connected thereto; (b) a first passageway extending along the device for providing high pressure gas to the operating member, the first passageway including a primary Joule Thomson heat exchanger in the form of a primary orifice located on the first passageway for enabling expansion of gas within the hollow of the operating member, thereby providing a desired temperature to the surface of the operating member; (c) a second passageway extending through the length of the housing member for evacuating gas from the operating tip to atmosphere; (d) a third passageway extending along a portion of the device and including a secondary Joule Thomson heat exchanger for providing a desired temperature to gas flowing through the first passageway. Method and device according to the present invention enable to form durable transmyocardial channels without causing considerable trauma to the myocardial tissue.

12 Claims, 2 Drawing Sheets

Page 2 …

METHOD AND DEVICE FOR TRANSMYOCARDIAL CRYO REVASCULARIZATION

FIELD AND BACKGROUND OF THE INVENTION

The present invention relates to method and device for trans myocardial cryo revascularization. More particularly, the present invention relates to a method of conducting trans myocardial revascularization by means of a cryosurgery device. Further, the present invention relates to a cryosurgery device including a plurality of Joule-Thomson heat exchangers which enables to effectively conduct such revascularization procedure.

Trans myocardial revascularization (TMR) procedures including the formation of transmyocardial channels extending from the epicardium to the left ventricular cavity are well known in the art. Such TMR procedures are currently performed by using $CO_2$ laser or Holmium:YAG laser and are generally known as TMLR procedures.

Various studies have been conducted so as to determine whether such TMLR channels provide significant myocardial perfusion by allowing blood to flow therethrough from the left ventricular chamber into the myocardium.

Histological examinations have revealed that such channels do not provide significant myocardial perfusion. Rather, the channels undergo significant morphologic changes within two weeks, wherein epicardial and endocardial scars appear at the ends of the channels, and wherein the channels are invaded with granulation tissue containing capillaries and lacunar spaces filled with fibrin and red blood cells. After two weeks, the channels are obscured with massive healing response induced by the infraction so that no definitive channels are identified within the healing myocardium.

Thus, it seems that the TMLR (trans myocardial laser revascularization) method fails to provide durable transmyocardial channels and thereby fails to provide significant myocardial perfusion therethrough.

Rather, the healing of the laser induced myocardial burns involves the formation of scar tissue accompanied by neovascularization, which neovascularization may explain the long term therapeutic effect of such TMLR method.

There is thus a widely recognized need for, and it would be highly advantageous to have, cryosurgery method and device for trans myocardial cryo revascularization which enable to form durable transmyocardial channels without causing considerable trauma to the myocardial tissue.

It would be further advantageous to have such method and device which enable to minimize bleeding, and to substantially eliminate the risk of thrombosis, aneurysms or rupture of major blood vessels.

It would be further advantageous to have such method and device which enable to minimize edema and inflammatory response. Further, it would be advantageous to have such method and device which do not completely denature proteins and which enable regeneration of nerve fibers following Wallerian degeneration.

It would be further advantageous to have such method and device which enable to predetermine the location, shape and size of a lesion, thereby minimizing damage to the surrounding area.

Cryosurgery devices including a Joule-Thomson heat exchanger for providing a surface having a fast changing temperature are disclosed in U.S. Pat. Nos. 5,522,870; 5,540,062; and 5,603,221.

However, none of these inventions provides a plurality of cooling and/or heating chambers for effectively pre-cooling and/or pre-heating the incoming gas before it communicates with the operating tip.

Further, none of these inventions provides a plurality of Joule-Thomson heat exchangers for efficiently and rapidly changing the temperature of gas within such chambers so as to efficiently and rapidly change the temperature of the operating tip.

There is thus a widely recognized need for, and it would be highly advantageous to have, a cryosurgery device having a plurality of cooling and/or heating chambers for effectively pre-cooling and/or pre-heating the incoming gas before it communicates with the operating tip.

It would be further advantageous to have such a device which includes a plurality of Joule-Thomson heat exchangers for efficiently and rapidly changing the temperature of gas within such chambers so as to efficiently and rapidly change the temperature of the operating tip.

SUMMARY OF THE INVENTION

According to the present invention there is provided a cryosurgery device, comprising:(a) an operating member having an operating surface and a hollow; and a housing member connected to the operating member; (b) a first passageway extending along the housing member and a portion of the operating member for providing high pressure gas to the operating member, the first passageway including a primary heat exchanging element having a primary orifice located on the first passageway for enabling expansion of gas within the hollow of the operating member, thereby providing a desired temperature to the surface of the operating member; (c) a second passageway extending through the length of the housing member for evacuating gas from the operating tip to atmosphere; (d) a third passageway extending along a portion of at least one of the housing member and the operating member, the third passageway being in heat-exchange communication with the first passageway, the third passageway including a secondary heat exchanging element for providing a desired temperature to gas flowing through the first passageway.

According to further features in preferred embodiments of the invention described below, a portion of the first passageway is enclosed within the third passageway, and the secondary heat exchanging element includes a secondary orifice located on the first passageway for enabling expansion of gas within the third passageway.

According to another embodiment, the device comprises a fourth passageway enclosed by at least a portion of the third passageway, the fourth passageway for providing high pressure gas to a selected portion of the device. The secondary heat exchanging element preferably includes a secondary orifice located on the fourth passageway for enabling expansion of gas into the third passageway.

According to yet another embodiment, the first passageway provides a first high pressure gas and the fourth passageway provides a second high pressure gas.

The fourth passageway may extend along the housing member and a portion of the operating member, and may further include a tertiary orifice for enabling expansion of the second high pressure gas within the hollow of the operating member.

The first passageway and the fourth passageway may include a plurality of orifices located along their length.

Further according to the present invention there is provided a method of performing trans myocardial revascularization, comprising: forming trans myocardial channels by cryoablating selected portions of the myocardial tissue. Specifically, a method according to the present invention preferably comprises: (a) providing a high pressure gas to a primary portion of an elongated operating device and creating a primary cryogenic pool at the operating tip of the device; and (b) inserting the operating tip through a patient's myocardium so as to cryoablate selected portions of the myocardium.

According to further features in preferred embodiments of the invention described below, the method further comprises: providing a high pressure gas to a secondary portion of the operating device and creating a secondary cryogenic pool at the secondary portion so as to precool the high pressure gas provided to the primary portion of the device.

Preferably, the operating tip is inserted through the epicardium into the myocardium of a patient. Alternatively, the operating device is substantially flexible and the operating tip is inserted through an artery into a ventricular chamber of the patient, preferably by means of a catheter, so as to form channels extending from the ventricular chamber into the patient's myocardium.

According to still further features of the preferred embodiments, the method further comprises: providing a second high pressure gas to the primary portion of the operating device for heating the operating tip so as to prevent sticking of the tip to the myocardial tissue. Such second high pressure gas may be also provided to the secondary portion of the device so as to heat the gas provided to the primary portion of the device.

The present invention successfully addresses the shortcomings of the presently known configurations by providing cryosurgery method and device for trans myocardial cryo revascularization which enable to form durable transmyocardial channels without causing considerable trauma to the myocardial tissue.

Specifically, the present invention addresses the shortcomings of the presently known configurations by providing such method and device which enable to minimize bleeding, and to substantially eliminate the risk of thrombosis, aneurysms or rupture of major blood vessels.

Further, such method and device enable to minimize edema and inflammatory response, do not completely denature proteins, and enable regeneration of nerve fibers following Wallerian degeneration.

Further, the present invention addresses the shortcomings of the presently known configurations by providing such method and device which enable to predetermine the location, shape and size of a lesion, thereby minimizing damage to the surrounding area.

Further, the present invention addresses the shortcomings of the presently known configurations by providing a cryosurgery device having a plurality of cooling and/or heating chambers for effectively pre-cooling and/or pre-heating the incoming gas before it communicates with the operating tip. Further, the present invention addresses the shortcomings of the presently known configurations by providing a cryosurgery device having a plurality of Joule-Thomson heat exchangers for efficiently and rapidly changing the temperature of gas within such chambers so as to efficiently and rapidly change the temperature of the operating tip.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of method and device for trans myocardial cryo revascularization. Specifically, according to the present invention there is provided a method of conducting trans myocardial revascularization by means of a cryosurgery device. Further, according to the present invention there is provided a cryosurgery device including a plurality of Joule-Thomson heat exchangers which enables to effectively conduct such revascularization procedure.

The principles and operation of apparatus and method according to the present invention may be better understood with reference to the drawings and the accompanying description.

Figure 1:
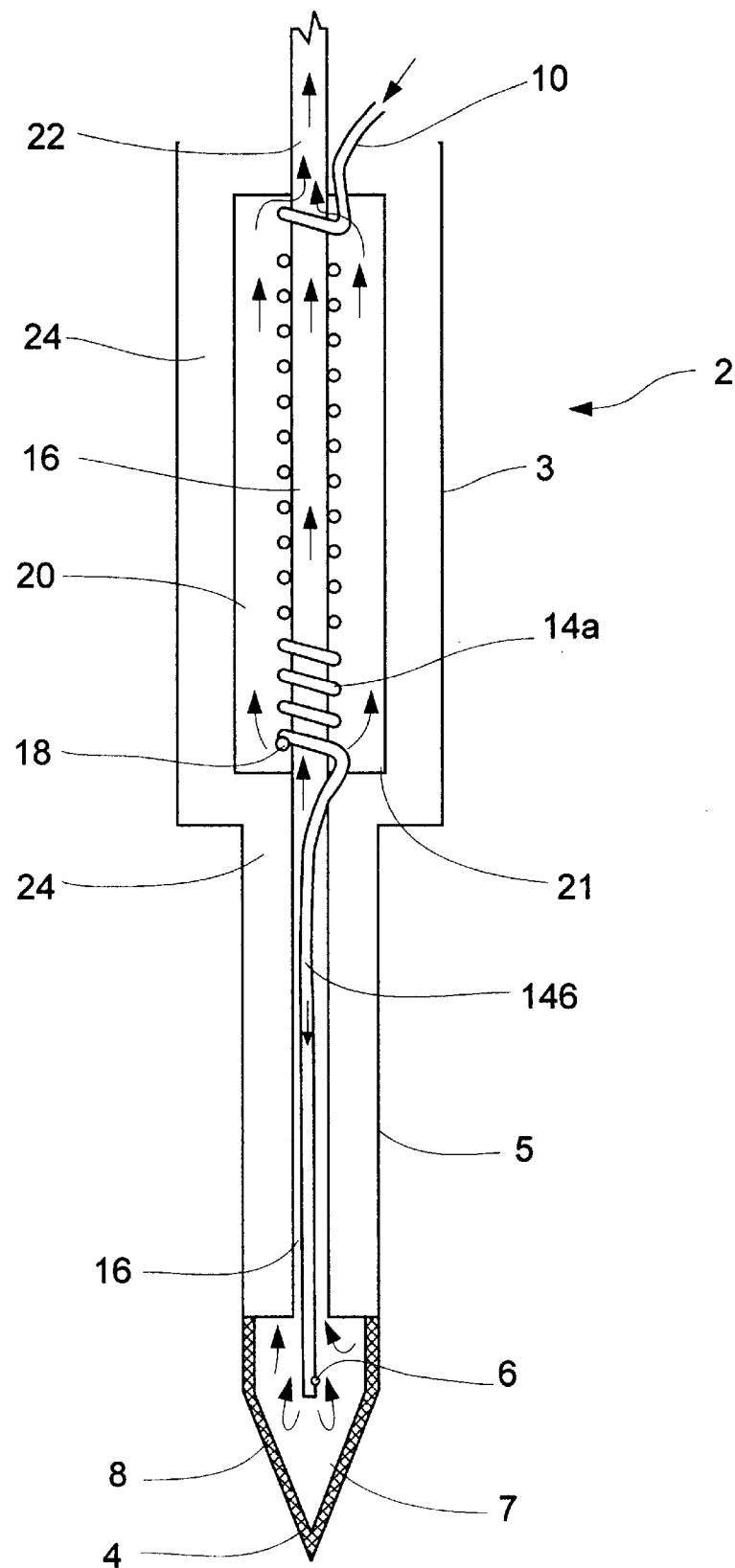
FIG. 1 is a schematic side view, partially in longitudinal section, of a cryosurgery device according to the present invention.

Referring now to the drawings, FIG. 1 illustrates a preferred embodiment of a cryosurgery device according to the present invention.

As shown in the figures, a cryosurgery device 2 according to the present invention preferably includes elongated housing 3 having a pointed operating tip 4 for penetrating through the epicardium and myocardium of a patient into a ventricular chamber. Operating tip 4 features a shape of a needle element for allowing a surgeon to effectively and accurately determine the site of insertion of operating tip 4 into the epicardium, and to appropriately directing the device through the patient's myocardium according to a desired and predetermined path. Operating tip 4 may feature various shapes and sizes so as to enable the surgeon to form transmyocardial channels of a predetermined diameter and shape, thereby minimizing damage to surrounding areas.

As shown in the figures, operating tip 4 is connected to elongated housing 3 by means of an elongated member 5 substantially thin in cross section for allowing insertion thereof through the patient's myocardium. According to another embodiment (FIG. 2), operating tip 4 is substantially elongated so as to allow effective cryoablation of tissues surrounding the tip when the tip penetrates the myocardium. Operating tip 4 and elongated member 5 preferably feature a diameter of between about 0.8 mm and about 1.6 mm so as to allow the formation of transmyocardial channels of substantially small diameter. Operating tip 4 preferably features a length of between about 2.5 cm and bout 3.5 cm for enabling effective cryoablation across the myocardium.

A cryosurgery device according to the present invention may feature any diameter and length adapted for carrying out cryosurgical procedures other than trans myocardial revascularization. For example, operating tip 4 and elongated member 5 may feature a diameter between about 0.5 mm and about 3 mm.

As shown in FIG. 1, a device according to the present invention includes a first passageways 10 extending along the length of the device for providing gas of high pressure to a heat exchanger located at operating tip 4, and a second passageway 16 for evacuating gas from the operating tip to atmosphere. First passageway 10 is preferably in the form of a substantially thin tubular element extending along elongated housing 3, elongated member 5, and a portion of operating tip 4. As shown in the figures, the portion of first passageway 10 extending along elongated housing 3 is preferably in the form of a spiral tube 14a wrapped around second passageway 16. The portion of first passageway 10 extending along elongated member 5 and portion of operating tip 4 is preferably in the form of a straight tube 14b received within second passageway 16. Further as shown in the figure, tube 14b preferably penetrates into second passageway 16 substantially adjacent the connection of elongated member 5 and housing 3.

Further, elongated housing 3 preferably includes a third passageway 20 enclosing first and second passageways 10 and 16, which third passageway forming a heat exchanging chamber for precooling or preheating gas flowing within spiral tube 14a before it arrives to operating tip 4. Third passageway 20 preferably merges with second passageway 16 at the upper end of elongated housing 3 to form a common passageway 22 for releasing gas to atmosphere.

As shown in the figures, the various passageways of the device are enclosed by an insulating chamber 24 extending along housing 3 and elongated member 5.

Preferably, a device according to the present invention provides effective cooling or heating by using Joule Thomson heat exchangers. Thus, first passageway 10 preferably includes a plurality of orifices for passage of high pressure gas therethrough so as to cool or heat selective portions of the device, depending on the type of gas used. Gases which may be used for cooling include argon, nitrogen, air, krypton, $CF_4$, xenon, $N_2O$, or any mixture of gases. Gases which may be used for heating include helium or any mixture of gases.

According to the embodiment shown in FIG. 1, a primary Joule Thomson heat exchanger is located at operating tip 4, which heat exchanger including: an orifice 6 located preferably at the end of straight tube 14b, and a chamber 7 defined by the inner walls of tip 4. When a high pressure gas such as argon expands through orifice 6 it liquifies so as to form a cryogenic pool within chamber 7 of operating tip 4, which cryogenic pool effectively cools surface 8 of operating tip 4. Surface 8 is preferably made of a heat conducting material such as metal for effectively freezing the myocardial tissue so as to produce the desired cryoablation effect. When a high pressure gas such as helium expands through orifice 6 it heats chamber 7 of operating tip 4, thereby heating surface 8 of the operating tip. Such heating of the operating tip may be used for preventing sticking of the device to the myocardial tissue.

A device according to the present invention preferably includes a plurality of Joule Thomson heat exchangers for effectively precooling or preheating the gas flowing within first passageway 10. According to the embodiment shown in FIG. 1, the device includes a secondary Joule Thomson heat exchanger located within housing 3, including: an orifice 18 located preferably at the lower end of spiral tube 14, and a chamber 21 defined by the inner walls of passageway 20. When a high pressure gas such as argon expands through orifice 18 it liquifies so as to form a cryogenic pool within chamber 21, which cryogenic pool effectively cools passageway 20, thereby precooling the gas flowing within spiral tube 14a. When a high pressure gas such as helium expands through orifice 18 it heats chamber 21 and passageway 20, thereby effectively preheating the gas flowing within spiral tube 14a.

Thus, gas flowing through spiral tube 14a is effectively pre-cooled or pre-heated by exchanging heat with third passageway 20. Furthermore, the gas flowing through spiral tube 14a and strait tube 14b exchanges heat with second passageway 16 which contains cooled (or heated) gas coming from operating tip 4.

A cryosurgery device according to the present invention enables to effectively and quickly produce the desired freezing effect and to quickly inverse from cooling to heating so as to prevent sticking of the operating tip to the tissue.

According to another embodiment (not shown), first passageway 10 may include a plurality of orifices located along spiral tube 14a and strait tube 14b. Further, a device according to the present invention may include a plurality of Joule Thomson heat exchangers for cooling or heating selected portions of the device, wherein each of the heat exchangers includes plurality of orifices.

Figure 2:
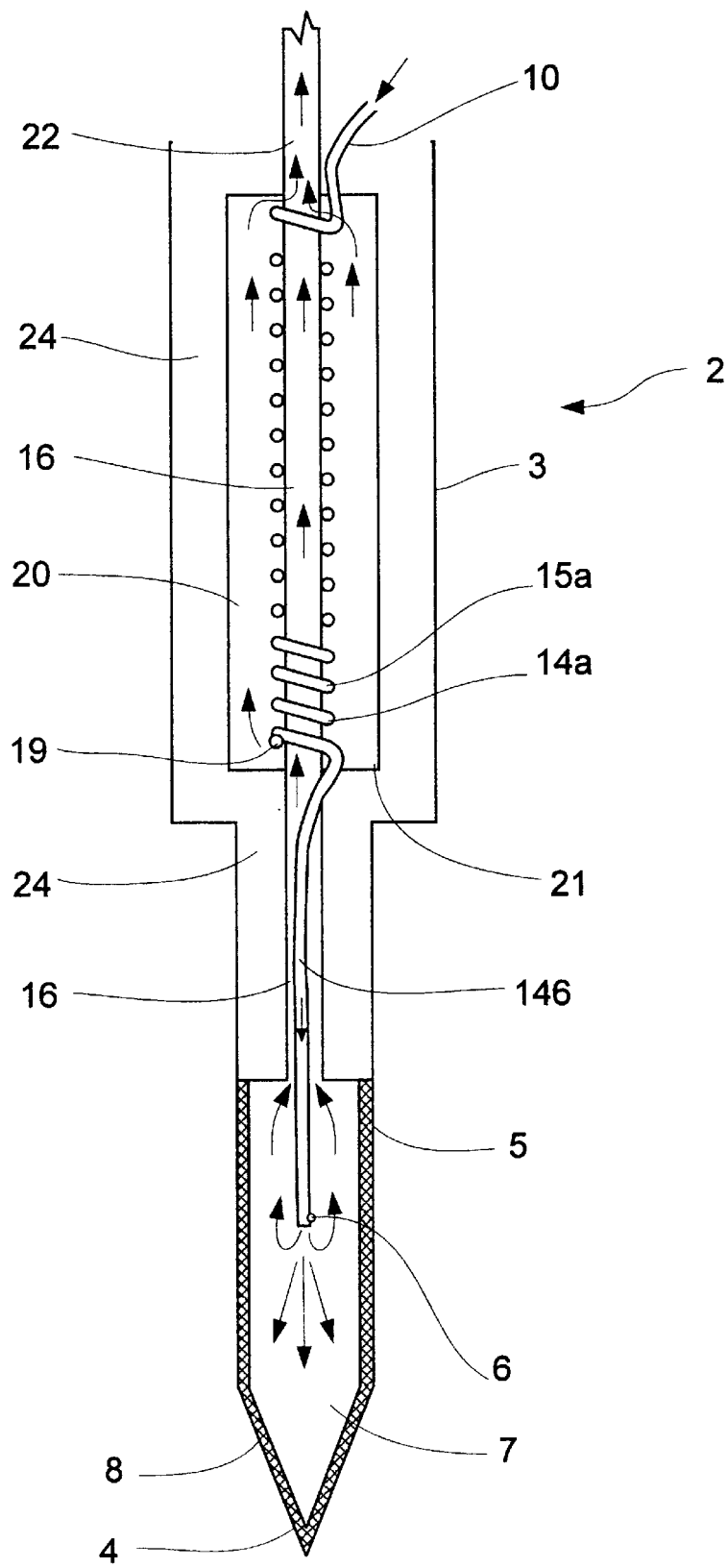
FIG. 2 is a schematic side view, partially in longitudinal section, of another embodiment of a cryosurgery device according to the present invention.

Referring now to FIG. 2, according to another embodiment the device may include a plurality of entering passageways of distinct lengths, each passageway for providing gas to a selected portion of the device. Thus, the device may include two entering passageways, 10 and 11, wherein passageway 10 ends nearby operating tip 4 and provides high pressure gas so as to selectively cool or heat chamber 7 and operating tip 4, and wherein passageway 11 ends at housing 3 and provides high pressure gas so as to selectively cool or heat chamber 21 and third passageway 20. Preferably, passageway 10 includes a spiral tube portion 14a extending along housing 3 and a straight tube portion 14b extending along elongated member 5 and having an orifice 6 located at its end. Passageway 11 preferably includes a spiral tube portion 15a extending along housing 3 and having an orifice 19 located at its end.

According to yet another embodiment (not shown), the device includes two entering passageways extending through the length of the device and ending nearby the operating tip, wherein one passageway provides a cooling gas such as argon and the other passageway provides a heating gas such as helium, and wherein each of the passageways includes a primary orifice for cooling or heating chamber 7 and operating tip 4, and a secondary orifice for cooling or heating chamber 21 and passageway 20.

The various portions of the cryosurgery device may be substantially rigid or substantially flexible.

According to a preferred embodiment, a flexible elongated cryosurgery probe may be inserted retrogradely through an artery into a ventricular chamber, preferably by means of a catheter, so as to form transmyocardial channels extending from the ventricular chamber to a predetermined depth within the myocardium.

Such an embodiment enables to perform minimally invasive trans myocardial revascularization procedures in a closed chest fashion and eliminates the need to perform an open lateral thoracotomy.

According to a preferred embodiment of the invention, the incorporation of video-assisted thoracoscopy allows to continuously monitor the trans myocardial revascularization procedure so as to accurately direct the flexible probe to predetermined sites at the patient's epicardium and to control the depth of penetration into the myocardium. Preferably, an endoscope and/or a miniature video camera is connected to housing 3 of the cryosurgery device by means of a connector element.

Method and device according to the present invention enable to create durable transmyocardial channels without causing considerable trauma to the myocardial tissue due to their anesthetic quality.

Thus, such method and device enable to minimize bleeding, and to substantially eliminate the risk of thrombosis, aneurysms or rupture of major blood vessels. Further, such method and device enable to minimize protein denaturation, edema formation and inflammatory response.

Further, such method and device enable regeneration of nerve fibers following Wallerian degeneration.

According to further aspects of the present invention, angiogenesis inducing factors may be incorporated to the cryogenic device or independently injected into the drilled channels so as to stimulate formation of new blood vessels. Such angiogenesis inducing factors may include growth factors such as VEGF (Vascular Endothelial Growth Factor). Preferably, the angiogenesis inducing factors include vectors carrying genes encoding for specific growth factors so as to allow slow release of such growth factors for a predetermined period of time.

Trans myocardial cryo revascularization method and device according to the present invention enables to appropriately regulate the angiogenesis process by ensuring effective gene transfer. It is well know in the art that the effectiveness of gene transfer depends on the ratio of infecting particles to infected cells, which ratio referred to as multiplicity of infection (m.o.i.), wherein low m.o.i. results in ineffective gene transfer and high m.o.i. results in toxicity and cells death. Method and device according to the present invention enable to precisely predict the dimensions of the trans myocardial channels, thereby enabling to accurately determine the amount of infecting vector particles which would produce a desired therapeutic effect.

Transmyocardial cryo revascularization method according to the present invention provides favorable conditions for gene transfer since it provides a low temperature environment for introducing the vector particles, thereby enabling to maintain the infectivity of the vector particles for substantially extended period of time, unlike the TMLR method which creates substantially hot environment.

Further, when using a method according to the present invention, blood from the ventricular cavity immediately freezes at the endocardial surface, thereby enabling substantially prolonged communication between the vector particles and the myocardial tissue, unlike the TMLR method wherein ventricular blood flows through the myocardium to the epicardial surface.

While the invention has been described with respect to a limited number of embodiments, it will be appreciated that many variations, modifications and other applications of the invention may be made.

What is claimed is:

1. A cryosurgery device, comprising:
   (a) an operating member having an operating surface and a hollow; and a housing member connected to said operating member;
   (b) a first passageway extending along said housing member and a portion of said operating member for providing high pressure gas to said operating member, said first passageway including a primary heat exchanging element having a primary orifice located on said first passageway for enabling expansion of said gas within said hollow of said operating member, thereby providing a desired temperature to said surface of said operating member;
   (c) a second passageway extending through the length of said housing member for evacuating gas from said operating member to atmosphere;
   (d) a third passageway extending along a portion of at least one of said housing member and operating member, said third passageway being in heat-exchange communication with said first passageway, said third passageway including a secondary heat exchanging element for providing a desired temperature to gas flowing through said first passageway and
   (e) a fourth passageway enclosed by at least a portion of said third passageway, said fourth passageway for providing high pressure gas to a selected portion of said device, and wherein said secondary heat exchanging element includes a secondary orifice located on said fourth passageway for enabling expansion of gas into said third passageway;

wherein said first passageway provides a first high pressure gas and said fourth passageway provides a second high pressure helium gas.

2. The device of claim 1, wherein a portion of said first passageway is enclosed within said third passageway, and wherein said secondary heat exchanging element includes a secondary orifice located on said first passageway for enabling expansion of gas within said third passageway.

3. The device of claim 1, wherein a portion of said first passageway is in the form of a spiral tube wrapped around said second passageway.

4. The device of claim 1, wherein a portion of said first passageway is enclosed by said second passageway.

5. The device of claim 1, further including an insulating chamber.

6. The device of claim 1, wherein said first passageway includes a plurality of orifices located along its length.

7. The device of claim 1, wherein at least one of said orifices is for allowing expansion of said high pressure gas within said third passageway.

8. The device of claim 1, wherein said high pressure gas is selected from the group consisting of:
   (a) argon;
   (b) nitrogen;
   (c) air;
   (d) krypton;
   (e) $CF_4$;
   (f) xenon; and
   (g) $N_2O$.

9. The device of claim 1, wherein said housing member and said operating member feature an elongated shape.

10. The device of claim 9, wherein said operating member features a diameter of between about 0.8 mm and about 1.6 mm.

11. The device of claim 1, wherein at least a portion of said device is substantially flexible.

12. The device of claim 1, wherein at least a portion of said device is substantially rigid.

* * * * *